United States Patent [19]

Falco

[11] Patent Number: 4,626,505
[45] Date of Patent: Dec. 2, 1986

[54] SELECTABLE MARKERS FOR YEAST TRANSFORMATION

[75] Inventor: Saverio C. Falco, Arden, Del.

[73] Assignee: E. I. Du Pont de Nemours and Company, Wilmington, Del.

[21] Appl. No.: 583,337

[22] Filed: Feb. 24, 1984

[51] Int. Cl.[4] .................... C12N 15/00; C12N 1/18; C12N 1/00; C12R 1/865

[52] U.S. Cl. .................... 435/172.3; 435/317; 435/256; 435/942; 935/28; 935/37; 935/69; 935/82; 935/84

[58] Field of Search .................... 435/172.3, 317, 256, 435/942; 935/28, 37, 69, 82, 84

[56] References Cited

U.S. PATENT DOCUMENTS 4,387,162 6/1983 Aigle et al. .................... 935/28
4,511,652 4/1985 Fogel et al. .................... 935/84

FOREIGN PATENT DOCUMENTS 2489364 3/1982 France .................... 935/84

OTHER PUBLICATIONS

Bollon, "Analysis of Yeast ILV 1 CIS Control and Domain Mutants", Molecular and General Genetics 177, p. 283–289 (1980).

Favre et al., "Expression of a Valine-Resistant Acetolactate Synthetase Activity Mediated by the ILVO and ILVG Genes of E. Coli k-12, Molecular and General Genetics 143(3), pp. 243–252 (1976), C.A. 85:89845e.

Carlson et al., "Two Differentially Regulated mRNAs with Different 5' Ends Encode Secreted and Intracellular Forms of Yeast Invertase Cell, 28(1), pp. 145–154 (1982).

Reipen et al., Current Genetics 6:189 (1982).
Rose et al., Proc. Natl. Acad. Sci. USA 78:2460 (1981).
Jiminez et al., Nature 287:869 (1980).
Cohen et al., Proc. Natl. Acad. Sci. USA 77:1078 (1980).
Fried et al., Proc. Natl. Acad. Sci. USA 78:238 (1981).
Rine et al., Proc. Natl. Acad. Sci. USA 80:6750 (1983).
Fogel et al., Proc. Natl. Acad. Sci. USA 79:5342 (1982).

Primary Examiner—Charles F. Warren
Assistant Examiner—John E. Tarcza

[57] ABSTRACT

Plasmid vectors capable of transforming Saccharomyces cerevisiae to phenotypes characterized by resistance to selective concentrations of sulfonylurea herbicides are disclosed.

30 Claims, 2 Drawing Figures

SELECTABLE MARKERS FOR YEAST TRANSFORMATION

BACKGROUND OF THE INVENTION

1. Technical Field

This invention relates to plasmid-borne genetic markers and related processes useful for introducing exogenous DNA to yeast strains, particularly Saccharomvces cerevisiae.

2. Description of the Prior Art

Selective modification of the genetic complement of organisms by recombinant DNA techniques has enabled efficient production of valuable proteins, introduction of new capabilities to recipient organisms, and optimization of existing characteristics of organisms. To date, these techniques have been primarily applied to bacteria. particularly Escherichia coli. However, eukaryotic organisms, especially yeasts such as Saccharomyces cerevisiae, can also be employed as recipients of recombinant DNA molecules. Certain strains of Saccharomvces, particularly those bred for use in the brewing and baking industries, are of considerable commercial importance. Optimization or modification of industrial yeast varieties by recombinant DNA techniques could significantly increase their value.

In a typical cloning experiment, a selected DNA segment is incorporated into an autonomously replicating DNA molecule known as a vector. In a process called transformation, a recipient cell population is contacted with a preparation of vector molecules under conditions permitting incorporation of vector molecules by recipient cells. If a vector molecule contains a "marker" gene capable of expression by the recipients, those cells which have actually incorporated a vector molecule can be identified. For example, if a vector contains a gene conferring resistance to a particular antibiotic, transformed cells will be identifiable by their ability to grow and multiply in the presence of the antibiotic. Alternatively. a vector molecule can comprise a gene complementing a mutation which has eliminated the capacity of the recipient strain to synthesize a particular nutrient (a condition known as auxotrophy). In this case, only those cells which have incorporated and expressed a vector-borne nutritional marker gene will grow and multiply in media lacking the nutrient.

Experiments involving transformation of wild-type or industrial yeast strains have been impeded by unavailability of suitable genetic markers for detection of transformants. Industrial yeast strains generally lack auxotrophic mutations, which would provide means for selecting transformed cells. Moreover, few suitable antibiotics or other growth-affecting compounds for which resistance phenotypes are available are now known. Several marker systems are summarized below.

Certain genes of bacterial origin have been successfully employed as selective markers in yeast. Reipen, et al., Current Genetics 6:189 (1982) disclose use of a gene encoding beta-lactamase, an antibiotic-inactivating enzyme derived from E. coli, as a selectable marker in transformation experiments involving Saccharomyces cerevisiae. This gene was effective, however, only when expressed under control of a promoter sequence derived from another yeast operon. Rose, et al., Proc. Nat. Acad. Sci. USA 78:2460 (1981), disclose fusion of an intact URA3 gene from S. cerevisiae and a beta-galactosidase gene from E. coli on a hybrid plasmid cloning vehicle. Yeast transformed with the hybrid plasmid expressed beta-galactosidase activity. Jiminez, et al., Nature 287:869 (1980) describe experiments in which S. cerevisiae was co-transformed with a yeast vector and a bacterial colicin derivative carrying a transposable element conferring resistance to 2-deoxystreptamine. a relatively potent inhibitor of protein synthesis. Cohen. et al., Proc. Nat. Acad. Sci. USA 77:1078 (1980) describe transformation of S. cerevisiae to chloramphenicol resistance With a chimeric plasmid bearing an E. coli chloramphenicol resistance determinant. Gritz, et al., Gene 25:179 (1983) disclose transformation of yeast with a hybrid plasmid containing an E. coli gene conferring selectable resistance to the antibiotic hygromycin-B.

Although hybrid plasmids comprising yeast and bacterial DNA fragments have been employed in the research setting, circumstances can be envisioned (e.g., production of new strains for food processing) in which it would be desirable to avoid introduction of bacterial DNA into a particular yeast strain. In such a case, a vector-borne selectable marker of yeast origin would be preferred. The following references disclose plasmids bearing dominant selectable markers of yeast origin.

Fried, et al., Proc. Nat. Acad. Sci. USA 78: 238 (1981) describe experiments in which S. cerevisiae resistant to a protein synthesis inhibitor, trichodermin, were produced by transformation of a sensitive host strain with a plasmid population containing a library of DNA fragments derived from a resistant yeast strain.

Another approach to construction of antibiotic- or inhibitor-resistant yeast phenotypes involves gene amplification, in which multiple copies of a gene encoding an enzyme targeted by a given inhibitor are introduced to the host cell. A resulting increase in enzyme activity can result in a selectable resistance phenotype. For example, Rine, et al., Proc. Nat. Acad. Sci. USA 80:6750 (1983) describe gene amplification experiments leading to S. cerevisiae transformants resistant to the growth inhibitors tunicamycin and compactin. Fogel, et al.. Proc. Nat. Acad. Sci. USA 79:5342 (1982) describe selection of copper-toxicity resistant S. cerevisiae from a recipient strain transformed with a library of random yeast genomic DNA fragments inserted in an appropriate vector. Restriction endonuclease cleavage and electrophoresis experiments indicated that resistant transformants contained plasmids comprising multiple copies of a natural variant allele mediating resistance to copper toxicity. In several cases, the resistance genes were integrated into yeast chromosomal DNA.

As the accelerating pace of development in this area indicates, new selective markers derived from yeast DNA, vectors bearing such markers, and processes for using such vectors are of acute interest as useful tools for genetic manipulation of yeast.

SUMMARY OF THE INVENTION

The present invention provides a plasmid vector adapted for transformation of a host strain of genus Saccharomyces, said vector comprising a first DNA segment capable of transforming sensitive cells to a phenotype characterized by resistance to selective concentrations of sulfometuron methyl, a sulfonylurea herbicide. This invention also provides methods of using these vectors, DNA segments comprising mutant alleles of the ILV2 locus of Saccharomyces cerevisiae, and plasmid vector/host systems adapted for expression of exogenous DNA in yeast of genus Saccharomvces.

DETAILED DESCRIPTION OF THE INVENTION

Figure 1:
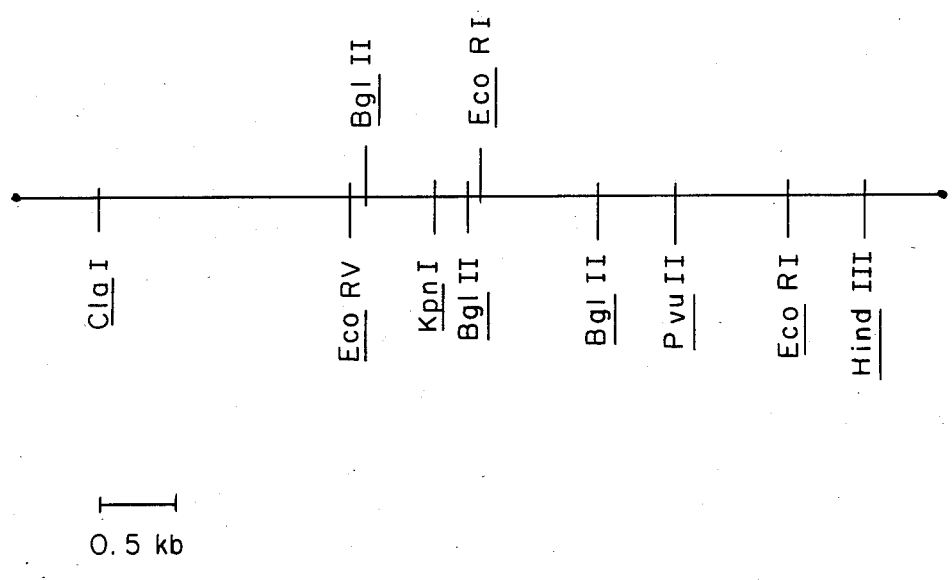
FIG. 1 is a partial restriction map of DNA segment CP2-4-10, which is allelic to the ILV2 locus in Saccharomyces cerevisiae. This segment provides a dominant selectable marker for yeast transformation when inserted in an appropriate plasmid vehicle.

Studies of the mechanism of action of certain sulfonylurea herbicides in bacteria and plants have indicated that these compounds inhibit the activity of acetolactate synthase (ALS), an enzyme which catalyzes the first common step in the biosynthesis of isoleucine and valine. Certain sulfonylurea herbicides are also growth inhibitors of yeast, for example, Saccharomyces cerevisiae. The sulfonylurea herbicide sulfometuron methyl inhibits growth of most strains of S. cerevisiae at a media concentration of 3 μg/mL. Sulfometuron methyl has the following structural formula:

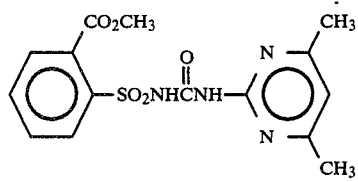

It has now been found that plasmid vector molecules, bearing mutant or wild-type alleles of the S. cerevisiae gene ILV2, can be constructed and used to transform sensitive host cells of wild-type or industrial yeast strains. The resulting phenotype is characterized by selectable resistance to concentrations of sulfometuron methyl which completely inhibit growth and multiplication of untransformed cells.

Definitions

As used throughout the specification, the following definitions apply. "plasmid vector", "plasmid" and "plasmid vehicle" each refer to a double-stranded DNA molecule capable of autonomous replication in a host cell of genus Saccharomyces, which molecule contains at least one restriction endonuclease cleavage site at which additional DNA can be inserted. Plasmid DNA useful in the present invention can be of yeast or bacterial origin. For research purposes, plasmids representing yeast/bacterial hybrids are preferred due to the ease with which plasmid DNA can be amplified in and extracted from certain bacterial strains. "Host cell" refers to a cell suitable or adapted for use as a recipient of plasmid vector DNA. "DNA segment" refers to a linear fragment of double-stranded deoxyribonucleic acid, which can be derived from any source. "Gene product" refers to a polypeptide obtained by transcription and translation of a selected DNA segment during protein synthesis. In the context of the present invention, "gene product" will usually refer to an enzyme or enzyme precursor. "Allele" refers to one of a group of genes which encode variants of a particular gene product and are located at a particular genetic locus. An allele of a yeast gene which has been isolated and is present on a plasmid vector is capable of integration by recombination into a particular locus of the yeast genome.

"Selective concentration" refers to a concentration of a growth-inhibitinq or antibiotic compound capable of inhibiting growth or multiplication of wild-type yeast or bacterial strains. Such a strain, or member cell thereof, is known as a "sensitive" strain or cell. "Resistance" refers to a capability of a strain or cell to grow and multiply in the presence of selective concentrations of inhibitor.

Sulfonvlurea Herbicides

Cells transformed with a plasmid vector of the present invention exhibit selectable cross-resistance to certain structurally related sulfonamide compounds effective as broad-spectrum preemergent and postemergent herbicides. As used herein in a generic sense, "sulfonylurea herbicides" refer to N-(heterocyclicaminocarbonyl)arylsulfonamide compounds exhibiting broad-spectrum herbicidal activity and low mammalian toxicity.

For purposes of the present invention, a "sulfonylurea herbicide" can be conveniently defined as any N-(heterocyclicaminocarbonyl)arylsulfonamide compound capable of inhibiting the growth of yeast strains sensitive to growth inhibition by the herbicide sulfometuron methyl, which compound simultaneously does not inhibit the growth of yeast strains specifically resistant to sulfometuron methyl.

Vectors and Host Strains

Yeast vectors within the scope of the present invention can be classified into two groups. A first, preferred group includes plasmids comprising a first DNA segment comprising a deoxyribonucleotide sequence allelic to a S. cerevisiae gene, which sequence encodes a gene product capable of conferring resistance to selective concentrations of sulfometuron methyl. This group includes, for example. plasmids comprising a mutant allele of ILV2, the S. cerevisiae locus coding for expression of ALS. Following transformation of an appropriate sensitive host strain, this mutant allele is expressed, resulting in production of an altered ALS enzyme which is resistant to inhibition by sulfometuron methyl. A particularly preferred class of vectors includes those comprising a second DNA segment comprising a fragment of DNA, normally exogenous to yeast, which has been selected for expression in a suitable host strain.

A second group of vectors within the scope of the present invention includes high copy number plasmids comprising a first DNA segment comprising one or more copies of a wild-type ILV2 gene. Following transformation of a suitable host strain with a vector of the second group. wild-type ALS enzyme is overproduced as a result of the presence of multiple copies of the wild-type gene. The resulting transformants are phenotypically resistant to media concentrations of sulfometuron methyl in the range of about 1 to 3 μg/mL.

Generally, DNA incorporated into vectors of the present invention can be of bacterial or yeast origin. Preferably, a vector constructed in accordance with the present invention incorporates both bacterial and yeast origins of replication, enabling the vector to be employed as a "shuttle vector" in both yeast e.g., S. cerevisiae) and bacteria (E. coli). As noted previously. certain applications could require use of a vector comprising only yeast DNA. In this case, bacterial sections of a given vector can be excised by known techniques. The presence of a yeast origin of replication permits autonomous plasmid replication in a yeast host cell. resulting in multiple copies of plasmid DNA. For this purpose, useful vectors are those containing an origin of replication derived from an endogenous yeast plasmid known as the "2 μm circle," or Scp 1. See Broach, in *The Molecular Biology of the Yeast Saccharomyces: Life Cycle and Inheritance*, Strathern et al., eds., (Cold Spring Harbor Laboratory, New York, 1981). In addition, the presence of DNA fragments allelic to yeast chromosomal genes provides a basis for stable integration of plasmid DNA into yeast chromosomal DNA by homologous recombination. Exploitation of this capability would be useful for introducing permanent, inheritable characteristics to industrial yeast varieties.

Figure 2:
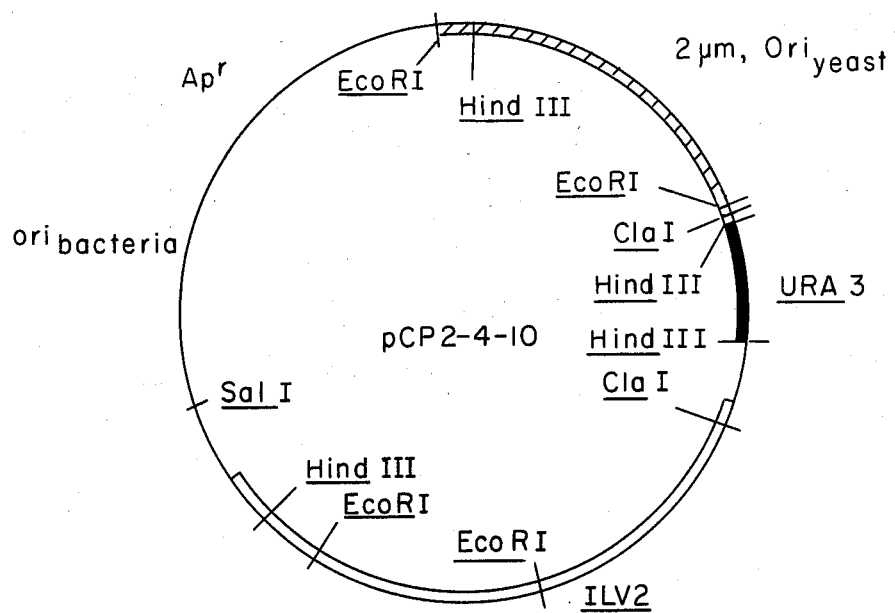
FIG. 2 is a schematic illustration of plasmid pCP2-4-10, which contains DNA segment CP2-4-10, in addition to an intact yeast URA3 gene and an E. coli gene conferring ampicillin resistance.

Preferred vectors are plasmids derived from the high copy number vector YEp24, which has been described by Botstein, et. al., *Gene* 8:17 (1979). A particularly preferred vector of the present invention is plasmid pCP2-4-10, which is illustrated in FIG. 2. As shown in FIG. 2, this plasmid contains a DNA segment derived from *E. coli* plasmid pBR322, comprising a gene conferring ampicillin resistance ($Ap^r$) and a bacterial origin of replication. In addition, this vector contains a yeast origin of replication derived from the 2 μm circle, a yeast URA3 gene, and DNA fragment CP2-4-10, which comprises a mutant ILV2 gene conferring selectable resistance to the sulfonylurea herbicide sulfometuron methyl.

Suitable yeast species for use in various embodiments of the present invention include those classified within the genus Saccharomyces, for example, *S. cerevisiae, S. bailii, S. bayanus, S. rouxii, S. sake*, and *S. tavarum*. Of the foregoing, *S. cerevisiae* is preferred. Within *S. cerevisiae*, strains having ATCC accession numbers ATCC 4921, (*S. cerevisiae* var. *elliosoideus*, a French wine yeast) and ATCC 7754 (NRRL Y-977, Fleischmann Baker's Yeast) represent particularly preferred industrial yeast strains.

The present inventlon is also directed to DNA segments comprising a deoxyribonucleotide sequence allelic to a *S. cerevisiae* gene, which sequence encodes a gene product resistant to selective concentrations of sulfonylurea growth inhibitors, for example, DNA fragments comprising mutant alleles of *S. cerevisiae* ILV2. One such fragment, approximately 5.6 kilobases in length, has been inserted into the high copy number plasmid YEp24 A restriction map of this fragment, designated CP2-4-10, is depicted in FIG. 1. The corresponding plasmid, pCP2-4-10, is described above and schematically illustrated in FIG. 2. This vector, inserted in *E. coli* host strain HB101, has been deposited in the American Type Culture Collection, Rockville, Md., USA, and assigned deposit accession number 39606. Samples of this strain are available to the public upon grant of a patent to the assignee. Other vectors and recipient strains representing various embodiments of the present invention are preserved in a deposit collection maintained by the Central Research and Development Department, Research Division, E. I. du Pont de Nemours and Company (Inc.). Experimental Station, Wilmington, Del., USA. to which requests for samples should be directed.

Vector Construction and Use

Methods of DNA manipulation, yeast transformation, preparation of growth media, and growth of yeast strains are well-known to those skilled in the art. Accordingly, such methods will not be detailed herein except by reference to specific embodiments of the present invention as set forth in the following Examples.

Useful background references covering relevant aspects of yeast genetics and manipulation of recombinant DNA include Sherman, et al., *Methods in Yeast Genetics* (Cold Spring Harbor Laboratory, New York. 1974); Davis, et al., *Advanced Bacterial Genetics: A Manual for Genetic Enoineering* (Cold Spring Harbor Laboratory, New York, 1980); and Maniatis, et al., *Molecular Cloning: A Laboratory Manual* (Cold Spring Harbor Laboratory, New York, 1982) The combined disclosures of the foregoing references are incorporated by reference herein.

In the followinq examples. all parts and percentages are by weight, and all degrees are Celsius, unless otherwise indicated.

EXAMPLES

Materials and Methods

Culture Media

Formulations employed for media (YEPD for non-selective growth; SD with appropriate supplements for selective growth and scoring of nutritional markers) are those disclosed by Sherman, et al., *Methods in Yeast Genetics*, (Cold Spring Harbor Laboratory, New York, 1974). Sporulation media contained 2% potassium acetate; 0.1% glucose; 0.25% nutrient extract, e.g., Bacto-yeast extract (Difco) and 1.5% agar, e.g., Bacto-agar (Difco). For addition to solid media, sulfometuron methyl, (molecular weight 364) was dissolved in acetone at 2 mg/mL and added to media at desired concentrations immediately prior to pouring into culture dishes.

DNA preparation

Plasmid DNA was prepared from *E. coli* by a rapid method substantially similar to that described by Rambach, et al., *Proc. Nat. Acad. Sci. USA* 74:5041 (1977); or by a cesium chloride density gradient method substantially similar to that disclosed by Davis, et al., *Advanced Bacterial Genetics: A Manual for Genetic Engineering* (Cold Spring Harbor Laboratory, New York, 1980). Yeast DNA was isolated by a method substantially similar to that disclosed by Falco, et al., *Cell* 29:573 (1982).

Yeast Transformation

Selected host strains of yeast were transformed by a method similar to that disclosed by Hinnen, et al., *Proc. Nat. Acad. Sci. USA* 75:1929 (1978), but with the following modification. Recipient cells were incubated with glusulase for 3 hours at 30° in 1 M sorbitol containing 1% mercaptoethanol and 0.1 M sodium citrate, pH 5.8, to form spheroplasts.

Assays for Acetolactate Synthase

This assay was performed substantially as described by Magee, et al.. *Eur. J. Biochem.* 3:502 (1968). Each reaction mixture contained. in a volume of 0.5 mL, 0.1 M potassium phosphate buffer. pH 8.0, 50 mM sodium pyruvate, 5 mM $MgSO_4$, 25 μg/mL thiamine pyrophosphate, and toluene-permeabilized cells.

Permeabilized cells were prepared from cultures in exponential phase (1 to $2 \times 10^7$ cells/mL) grown in SD media supplemented with nutrients. Cells were harvested by centrifugation, washed once in 0.1 M potassium phosphate buffer, pH 8.0, and resuspended in a small volume (one-twentieth original culture volume)

of 0.1 M potassium phosphate, pH 8.0, 25% v/v glycerol and 1 mM EDTA. Reagent grade toluene was added to a concentration of 10% v/v and the resulting suspension was mixed vigorously for 30 seconds and then incubated for 2 minutes at 30° in a waterbath. Cells were then kept on ice until needed. Total protein was measured by standard methods. Fifty microliters of permeabilized cells, containing 10 to 30 μg total protein, were used per reaction. Sulfometuron methyl was dissolved at 100 μg/mL in 0.1 M potassium phosphate, pH 8.0, or 2 mg/mL in acetone and added to reaction mixtures at desired concentrations.

Tubes containing assay mix were temperature equilibrated at 30° prior to addition of permeabilized cells to start each reaction. Reactions were stopped by addition of 0.1 mL 6N $H_2SO_4$ or 0.1 mL 2.5N NaOH. The tubes were heated for 15 minutes at 55° and then 0.4 mL of 0.5% creatine was added. followed by 0.4 mL of 4% α-naphthol in 2.5 N NaOH, with vigorous mixing after each addition. The tubes were heated again at 55° C. for 5 minutes and centrifuged to remove precipitate. Optical density at 530 nm was then determined. This assay measures acetoin. Acetolactate formed by enzymatic reaction is converted to acetoin by acidification in reactions stopped with $H_2SO_4$. Thus the difference in $OD_{530}$ readings of acid-stopped and base-stopped reactions is a measure of acetolactate formation over background acetoin formation.

EXAMPLE 1

Isolation and Characterization of Yeast Genomic DNA Segments Conferring Resistance to Sulfometuron Methyl To construct a plasmid containing yeast ILV2, three yeast genomic DNA libraries were constructed in high copy number plasmid YEp24 by the method described by Carlson, et al., Cell 28:145 (1982). This vector contains wild-type yeast gene URA3 for selection of transformants from a ura3 recipient strain. and a bacterial β-lactamase gene, for selection for ampicillin resistance in bacterial hosts. Fragments of yeast DNA resulting from partial digestion with restriction endonuclease Sau 3A1 were inserted into a Bam H1 site of plasmid YEp24 substantially as described by Botstein, et al., Gene 8:17 (1979). As previously noted, YEp24 is known to exist in yeast cells in multiple copies.

S. cerevisiae strains FY138 (α aas3 his4 ura3-50) and FY139 (α aas3 his4 lys2 ura3-50) were transformed to uracil prototrophy with the libraries described above. Approximately 10,000 Ura+ transformants were selected, pooled and spread at a concentration of approximately $1 \times 10^6$ cells per plate on media lacking uracil and including sulfometuron methyl at a minimal inhibitory concentration of 1 μg/mL.

Colonies resistant to sulfometuron methyl appeared at a frequency of approximately 1 to 5 per $10^4$ transformants. Twelve clones, two from each library in each strain background, were selected and further characterized.

In order to determine whether the sulfometuron methyl resistance determinant was plasmid-borne. the inherent instability of the plasmids was exploited. Segregants that were Ura−, due to loss of plasmid, were isolated from each clone, following growth on non-selective media. In the case of 10 of the 12 clones thus analyzed, all Ura− segregants were also sensitive to selective concentrations of sulfometuron methyl, indicating that the resistance determinant was plasmid borne. To confirm this observation, and to isolate cloned plasmids. DNA was prepared from the foregoing 10 yeast transformants and used to transform E. coli strain HB101 to ampicillin resistance. Plasmid DNA was prepared from bacterial transformants derived from each of the 10 yeast DNA preparations. When introduced back into yeast by transformation, eight of the ten plasmids yielded all Ura+ transformants which were also resistant to sulfometuron methyl. Restriction enzyme mapping of the eight bacterial plasmid preparations revealed 4 different plasmids; one, pCP2-4, was isolated once; two, pCP2-2 and pDP3-1 were isolated twice; and one, pCP1-1. was isolated three times. Yeast genomic DNAs inserted in plasmids pCP2-2, pDP3-1 and pCP1-1 are related, having a number of common restriction fragments; a yeast genomic DNA fragment carried by pCP2-4 is unrelated to the other three.

Toluene-permeabilized cell samples of plasmid-bearing strains were then assayed for ALS to determine whether this enzyme was overproduced. A four- to five-fold increase in ALS specific activity was seen in strain FY138 carrying plasmid pCP2-4. This result suggested that pCP2-4 carried an intact structural gene encoding ALS, ILV2. Only a slight increase in ALS activity was observed in extracts of strains harboring the remaining plasmids.

To prove that plasmid pCP2-4 carried an intact yeast ILV2 gene, mutations were sought which would result in production of altered ALS enzyme activity. Mutants of strain FY138 carrying pCP2-4 were selected on media lacking uracil and including sulfometuron methyl at a higher selective concentration (30 μg/mL). (The presence of pCP2-4 in FY138 confers sulfometuron methyl resistance only to a concentration of 3 μg/mL). Six independently isolated spontaneous, high-level resistant mutants were obtained and characterized.

To establish that the foregoing mutations were plasmid-borne, Ura− segregants were isolated as described above. For each mutant, every Ura− segregant (which indicates loss of plasmid) was sensitive to sulfometuron methyl. DNA isolated from these mutant clones was then used to transform E. coli strain HB101 to ampicillin resistance. Plasmid DNA was then prepared from bacterial cultures of the resulting transformants. When reintroduced into yeast strain FY138, these plasmids yielded transformants which were resistant to 30 μg/mL sulfometuron methyl, demonstrating that high-level resistance determinants were plasmid-borne.

The ALS activity of strain FY138 recipients carrying each of these mutant plasmids was assayed in the presence and absence of 0.8 μM sulfometuron methyl. Data shown in Table 1, below, indicate that each plasmid mutation leads to a large increase in ALS activity resistant to inhibition by sulfometuron methyl. These results support a conclusion that pCP2-4 carries an intact ILV2 gene.

TABLE 1

| Sulfometuron Methyl (SM) Resistant ALS Activity Due to Plasmid-borne Mutations | |
|---|---|
| Plasmid | Percent ALS Activity Resistant to 0.8 μM SM |
| None | 7 |
| YEp24 | 9 |
| pCP2-4 | 4 |
| pCP2-4-5 | 72 |
| pCP2-4-8 | 70 |
| pCP2-4-10 | 100 |
| pCP2-4-11 | 77 |

TABLE 1-continued

Sulfometuron Methyl (SM) Resistant ALS Activity
Due to Plasmid-borne Mutations

| Plasmid | Percent ALS Activity Resistant to 0.8 μM SM |
|---|---|
| pCP2-4-13 | 85 |
| pCP2-4-15 | 83 |

EXAMPLE 2

Transformation of Industrial Yeast Strains

Plasmid pCP2-4-10. isolated as described above, was used to transform industrial *S. cerevisiae* strains ATCC 7754 and ATCC 4921 to a phenotype resistant to sulfometuron methyl. The transformation protocol was substantially similar to that previously described, and transformants resistant to 30 μg/mL sulfometuron methyl were selected. Growth of untransformed wild-type strains was completely inhibited at this concentration. The optimum period of incubation with glusulase for producing spheroplasts was determined to be approximately 3 hours.

Loss of sulfometuron methyl resistance resulting from transformation occurred in 20 to 80 percent of cells grown approximately 25 generations on non-selective media, indicating that the gene conferring resistance was plasmid-borne.

The resulting industrial transformants were resistant to other, structurally related sulfonylurea growth inhibitors in addition to sulfometuron methyl. These inhibitors included N-[(4-methoxy-6-methyl-pyrimidin-2-yl)aminocarbonyl]-2-nitrobenzenesulfonamide; N-[(4,6-dimethoxy-pyrimidin-2-yl)-aminocarbonyl]-2-methyl-thiobenzenesulfonamide; and 2-[[(4-chloro-6-methoxypyrimidine-2-yl)amino carbonyl]aminosulfonyl]benzoic acid, ethyl ester.

The foregoing disclosure illustrates particular embodiments of the present invention. However, the invention is not limited to the precise construction herein disclosed but rather encompasses all modifications or embodiments thereof within the scope of the following claims.

I claim:

1. A plasmid vector adapted for transformation of a host strain of qenus Saccharomyces, said vector comprising a first DNA segment capable of transforminq sensitive cells to a phenotype characterized by resistance to selective concentrations of sulfometuron methyl.

2. A plasmid vector according to claim 1, wherein the host strain is *Saccharomvces cerevisiae*.

3. A plasmid vector according to claim 2, wherein said vector is a multicopy plasmid.

4. A plasmid vector according to claim 3, wherein the first DNA segment comprises at least one deoxyribonucleotide sequence corresponding to a wild-type *Saccharomyces cerevisiae* ILV2 gene.

5. A plasmid vector according to claim 2, wherein the first DNA segment comprises a deoxyribonucleotide sequence allelic to a *Saccharomvces cerevisiae* gene, which sequence encodes a gene product capable of conferring resistance to selective concentrations of sulfometuron methyl.

6. A plasmid vector according to claim 5, wherein the sequence is a mutant allele of ILV2, a *S. cerevisiae* structural gene encoding acetolactate synthase.

7. A plasmid vector according to claim 6, wherein the mutant allele is dominant with respect to a wild-type *S. cerevisiae* gene.

8. A plasmid vector according to claim 7, additionally comprising plasmid DNA derived from *S. cerevisiae*.

9. A plasmid vector according to claim 8, additionally comprising a yeast origin of replication.

10. A plasmid vector according to claim 9, additionally comprising a bacterial origin of replication.

11. A plasmid vector according to claim 10, wherein the bacterial origin of replication is derived from pBR322.

12. A plasmid vector accordinq to claim 11, wherein said plasmid vector is derived from plasmid YEp24.

13. A plasmid vector according to claim 12, plasmid pCP2-4-10.

14. A plasmid vector according to claim 13, wherein the host strain is *S. cerevisiae* ATCC 7754.

15. A plasmid vector according to claim 9, wherein the yeast origin of replication is derived from an endogenous yeast plasmid.

16. A plasmid vector according to claim 8, additionally comprising a second DNA segment comprising a deoxyribonucleotide sequence normally exogenous to *S. cerevisiae*.

17. A plasmid vector according to claim 5, wherein the selective concentration is 3 μg/mL.

18. A plasmid vector according to claim 17, wherein the selective concentration is 30 μg/mL.

19. A plasmid vector/host strain system for expression of DNA normally exogenous to *S. cerevisiae*, said system comprising a suitable *S. cerevisiae* host strain and a plasmid vector according to claim 5.

20. A plasmid vector/host strain system according to claim 19, wherein the host strain is *S. cerevisiae* ATCC 7754 and the plasmid vector is pCP2-4-10.

21. A transformant *S. cerevisiae* cell comprising a plasmid according to claim 5.

22. A transformant *S. cerevisiae* cell cekkm comprising a plasmid according to claim 1.

23. A method of introducing DNA normally exogenous to *S. cerevisiae* to a *S. cerevisiae* host cell, comprising:
    (a) transforming a suitable host strain population with a plasmid vector of claim 1;
    (b) exposing said population to a selective concentration of sulfometuron methyl or other sulfonylurea herbicide; and
    (c) selecting transformants capable of growth in the presence of the selective concentration of the herbicide.

24. A method according to claim 23, wherein the plasmid vector is as defined in claim 5.

25. A method according to claim 24, wherein the sulfonylurea growth inhibitor is sulfometuron methyl and the selective concentration is 30 μg/mL.

26. A method according to claim 25, wherein the plasmid vector is plasmid pCP2-4-10.

27. A DNA segment comprising a deoxyribonucleotide sequence allelic to a *Saccharomyces cerevisiae* gene, which sequence encodes a gene product resistant to selective concentrations of sulfometuron methyl.

28. A DNA segment according to claim 27, wherein the sequence is a mutant allele of ILV2, a *S. cerevisiae* structural gene encoding acetolactate synthase.

29. A DNA segment according to claim 28, wherein the sequence is fragment CP2-4-10.

30. A transformant *S. cerevisiae* cell comprising plasmid pCP2-4-10.

* * * * *